United States Patent [19]
Bolton

[11] Patent Number: 5,980,954
[45] Date of Patent: Nov. 9, 1999

[54] TREATMENT OF AUTOIMMUNE DISEASES

[75] Inventor: Anthony E. Bolton, Toronto, Canada

[73] Assignee: Vasogen Ireland Limited, Ireland

[21] Appl. No.: 08/754,348

[22] Filed: Nov. 22, 1996

Related U.S. Application Data

[63] Continuation-in-part of application No. 08/352,802, Dec. 1, 1994, Pat. No. 5,591,457, which is a continuation-in-part of application No. 07/941,327, Sep. 4, 1992, abandoned, which is a continuation-in-part of application No. 07/832,798, Feb. 7, 1992, abandoned.

[30] Foreign Application Priority Data

Aug. 22, 1996 [GB] United Kingdom ................. 96176110

[51] Int. Cl.$^6$ ..................................................... A01N 39/00
[52] U.S. Cl. ........................... 424/613; 424/810; 422/24; 422/44; 422/45; 422/46; 604/4
[58] Field of Search .............................. 424/93.21, 278.1, 424/829, 613, 810; 435/372, 375, 377; 604/4; 422/24, 44, 45, 46

[56] References Cited

U.S. PATENT DOCUMENTS

| | | | |
|---|---|---|---|
| 3,715,430 | 2/1973 | Ryan | 424/127 |
| 4,632,980 | 12/1986 | Zee et al. | 530/380 |
| 4,831,268 | 5/1989 | Fisch et al. | 250/432 |
| 4,968,483 | 11/1990 | Mueller et al. | 422/520 |
| 5,052,382 | 10/1991 | Wainwright | 128/202.25 |

OTHER PUBLICATIONS

D. Baran et al. (associates) "Technical Report and Clinical Update" Mueller Medical International Inc., Oakville, Ontario, Canada, Sep. 1990.

*Primary Examiner*—Christina Y. Chan
*Assistant Examiner*—Patrick Nolan
*Attorney, Agent, or Firm*—Ridout & Maybee; Robert G. Hirons

[57] ABSTRACT

An autoimmune vaccine is provided for administration to human patients to alleviate the symptoms of autoimmune diseases such as rheumatoid arthritis. The vaccine comprises an aliquot of the patient's blood, containing, inter alia, leukocytes having upregulated expression of various cell surface markers and lymphocytes containing decreased amounts of certain stress proteins. It is produced by subjecting the blood aliquot extracorporeally to certain stressors, namely oxidizing agents, UV radiation and elevated temperature.

12 Claims, 1 Drawing Sheet

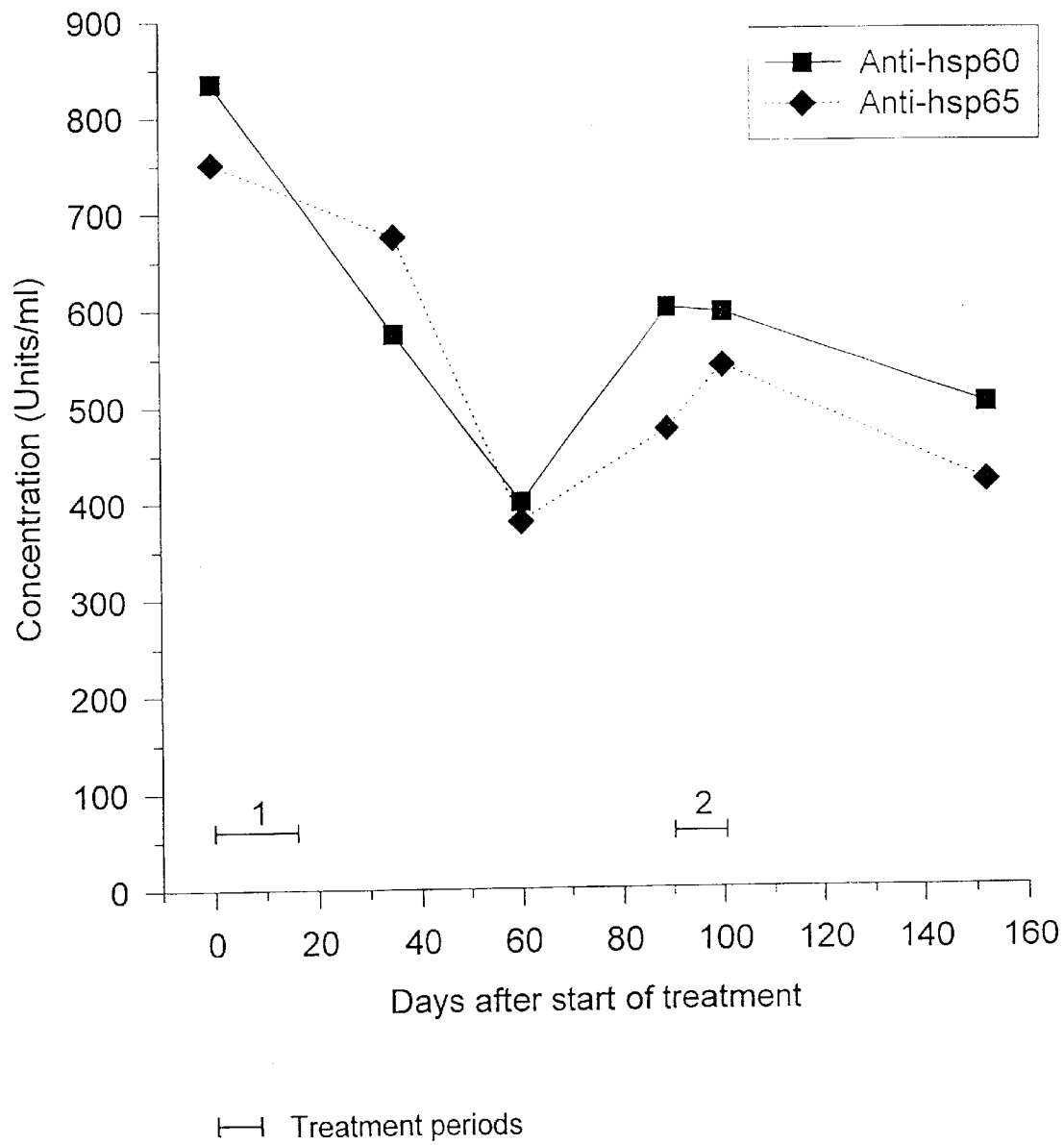

TREATMENT OF AUTOIMMUNE DISEASES

This application is a continuation-in-part of U.S. patent application Ser. No. 08/352,802 filed Dec. 1, 1994 and now U.S. Pat. No. 5,591,457, which is in turn a continuation-in-part of U.S. patent application Ser. No. 07/941,327 filed Sep. 4, 1992 and now abandoned, which was in a turn a continuation-in-part of U.S. patent application Ser. No. 07/832,798 (now abandoned) filed Feb. 7, 1992.

FIELD OF THE INVENTION

This invention relates to vaccines, their preparation and use in medical treatments. More particularly, it relates to treatments for alleviating autoimmune diseases and their symptoms, to a vaccine useful therein, and to processes for preparing and using such a vaccine.

BACKGROUND OF THE INVENTION

Autoimmune diseases include rheumatoid arthritis, graft versus host disease, systemic lupus erythromatosis (SLE), scleroderma, multiple sclerosis, diabetes, organ rejection, inflammatory bowel disease, psoriasis, and other afflictions. It is becoming increasingly apparent that many vascular disorders, including atherosclerotic forms of such disorders, have an autoimmune component, and a number of patients with vascular disease have circulating auto antibodies. Autoimmune diseases may be divided into two general types, namely systemic autoimmune diseases (exemplified by arthritis, lupus and scleroderma), and organ specific (exemplified by multiple sclerosis, diabetes and atherosclerosis, in which latter case the vasculature is regarded as a specific organ).

In general terms, a normally functioning immune system distinguishes between the antigens of foreign invading organisms (non-self) and tissues native to its own body (self), so as to provide a defence against foreign organisms. Central to the proper functioning of the immune system, therefore, is the ability of the system to discriminate between self and non-self. When a patient's immune system fails to discriminate between self and non-self and starts to react against self antigens, then an autoimmune disorder may arise.

The causes responsible for the reaction of an affected person's immune system against self are not fully understood, and several different theories have been put forward. The immune response to an antigen is triggered by the interaction of the antigen with receptors of predetermined specificity on certain lymphocytes. It is believed that, at an early stage in development of the immune system, those lymphocytes with receptors recognizing self antigens are recognized and eliminated from the body's system by a process of deletion. Alternatively, or in addition, such self-reactive lymphocytes may be controlled by the suppression of their activities. Both mechanisms probably occur.

The immune system of normal healthy individuals is able to identify and to react against a family of proteins which are highly conserved in nature (i.e. they have a similar structure throughout all living organisms). This family of proteins is called the stress or heat-shock proteins (HSP), and they are grouped according to their approximate molecular weights. Members of the HSP family include the HSP60 group, including, among others, proteins in the molecular weight range 50 to 100 kilodaltons. Increased production of HSP's was first identified as a response to heat stress, but this now appears to be part of a general response to a variety of cell stresses. HSPs are normally located within cells, and their function appears to be the stabilization of the structure of various proteins in stressed cells, so as to protect the cell from the protein denaturing effects of various stressors. However, it is likely that HSPs have a number of other functions which are, as yet, not fully understood. Heat shock proteins, HSP's, are discussed in some detail by William J. Welch, in an article in "Scientific American", May, 1993, page 56.

One group of the family of HSP's, the HSP 60 group, contains proteins which show about 50% identity between bacterial cells and human cells. Infection with bacteria containing HSP 65 results in an immune response in healthy humans against the bacterial HSP65, evidenced by the production of anti-HSP65 antibodies. Thus, a healthy immune system appears to be able to identify and react against self-like antigens.

In certain pathologies, for example many autoimmune diseases such as rheumatoid arthritis and scleroderma, patients also show the presence of antibodies to HSP 65. In the past, this has led to conclusions that autoimmune diseases result from bacterial infection. Now it seems likely that autoimmune diseases are associated with an inappropriate control of the autoimmune response. In other words, it is possible that the antibodies to HSP 65 result from an autoimmune reaction initiated by HSPs from the body itself, but one which has been improperly controlled. In such cases, therefore, it should be possible to control an inappropriate autoimmune response, by stimulating the body's natural immune control mechanisms, using a particular and specific method of vaccination.

To stimulate the body's immune response, a vaccine is required which will, upon injection into the host body, enable the host immune system to present the antigens contained in the vaccine to cells of the host immune system. Antigen presentation is performed by antigen presenting cells.

A vaccine to treat autoimmune diseases should contain antigens or fragments thereof (peptides) that will activate the body's immune control mechanisms present. In addition, the antigens (peptides) should be present in a form which can be recognized by the host immune system when the vaccine is introduced into the host. Certain of the antigens may be present on intact cells. The objective of such a vaccination is to activate regulatory immune pathways, particularly those controlling autoimmune responses, thereby downregulating the autoimmune response.

The particular antigens which will activate the control mechanisms of a mammalian autoimmune system are not fully understood. It is however recognized that they may include antigens derived from lymphocyte receptors, which may function to stimulate control mechanisms, to inhibit those lymphocytes which cause pathological autoimmune responses in the patient. They may also include HSPs, such as the HSP 60 group of proteins, and leucocyte surface molecules such as those of the Major Histocompatibility Complex (MHC) including MHC Class II molecules. MHC Class II molecules function physiologically to present peptides to $CD4^+$ T-cells as part of the immune response.

It is important that the lymphocyte receptors and other cell-derived molecules for vaccination of an auto-immune suffering patient be derived from cells obtained from the same patient, since this system will contain the autoimmune specificity. Receptors on other leucocytes in the blood may alternatively or additionally be important in a proposed vaccination process. The use of such a system as the basis of a vaccine may be considered analogous to the use of a particular viral antigen as a vaccine to treat and prevent disease caused by that virus. A vaccine for treating an autoimmune disease should, therefore, be prepared from a sample of the patient's own blood. Such a vaccine may be described as an autovaccine.

For antigens to be effective in stimulating (or inhibiting) the immune system, the antigens should be presented to immune cells of the host system by antigen-presenting cells, which are naturally present in the body. Many of the antigen-presenting cells are phagocytes, which attach to the antigens, engulf them by phagocytosis, and break them down or process them. The preparation of such an autovaccine should include a process whereby the lymphocytes and other leucocytes in the vaccine, which may be a source of antigens, are modified into a form whereby they are likely to be phagocytosed by phagocytic antigen-presenting cells upon re-injection into the patient, so that the antigens or effective residues thereof are presented on the surface of an antigen-presenting cell. Then they can effect a controlling mechanism on the immune system, either inhibitory or stimulatory.

During the normal growth period of a mammalian body, tissues become reshaped with areas of cells being removed. This is accomplished by the cells' undergoing a process called programmed cell death or apoptosis, the apoptotic cells disintegrating and being phagocytosed while not becoming disrupted.

BRIEF REFERENCE TO THE PRIOR ART

U.S. Pat. No. 3,715,430 Ryan relates to a method and apparatus for producing substantially pure oxygen having a controlled content of ozone and higher oxygen polymers. The purified oxygen gas is exposed to ultraviolet light in a wavelength of 2485 to 2537 angstrom units in order to produce 5 to 500 parts per million of ozone and higher oxygen polymers in the gas mixture. Ryan indicates that the gas produced in this manner is non-irritating to the human body and may be intravenously injected into the blood stream for therapeutic use.

U.S. Pat. No. 4,632,980 Zee et al. discloses a method of freeing blood and blood components of enveloped viruses by contacting the blood or blood product in an aqueous medium with an enveloped virus inactivating amount of ozone. The treatment is carried out at a temperature of 4° to 37° C., and an ozone concentration of 1–100 ppm.

U.S. Pat. No. 4,831,268 Fisch et al. provides a method for the radiation of blood to prevent arteriosclerosis related heart and vascular diseases caused by disturbances in the fat exchange. The disclosed process involves irradiating the blood in a blood conducting tube with radiation having an intensity of from about 1 mWcm$^{-2}$ to 10 mWcm$^{-2}$ in a wavelentgh range of from about 300 to 600 nm.

U.S. Pat. No. 4,968,483 Mueller et al. describes an apparatus for oxygenating blood, by treating an aliquot of a patient's blood, extracorporeally, with an oxygen/ozone mixture and ultraviolet light, at a controlled temperature. The apparatus is proposed for use in haematological oxidation therapy.

U.S. Pat. No. 5,052,382 Wainwright discloses an apparatus for the controlled generation and administration of ozone. The apparatus includes a generator for generating ozone, a monitor for monitoring the ozone production, a dosage device for providing a predetermined amount of ozone administration, and a computer control device for controlling the operation of the apparatus. The patent further discloses that administration of ozone to patients is known for the treatment of viral and bacterial infections, as well as for the treatment of external sores and wounds.

SUMMARY OF THE INVENTION

It is an object of the present invention to provide a novel autovaccine useful in the alleviation of symptoms of at least one autoimmune disease.

It is a further object of the present invention to provide a novel process for the preparation of such an autovaccine.

It is a further and more specific object of the present invention to provide a novel treatment for the alleviation of the symptoms of at least one autoimmune disease in a human patient suffering therefrom.

Accordingly, the present invention provides, from a first aspect, an autovaccine for treatment of an autoimmune disease in a mammalian patient, and derived from an aliquot of the autoimmune patient's own blood. The autovaccine is characterized by the presence therein, in comparison with the normal blood of the autoimmune patient, of at least one of the following characterizing features:

increased numbers of lymphocytes and other leucocytes, exhibiting a condensed apoptotic-like morphology;

a release of specific proteins from the cell surface of the blood leucocytes, including the MHC Class II molecule HLA-DR, resulting in a reduction in the number of cells expressing such surface proteins;

an upregulation in the expression of certain cell surface markers for example CD-11b, a component of the ligand for the cell adhesion molecule ICAM-1; and certain T-cell regulatory molecules;

an increase in the amount of heat shock protein HSP-60 in the plasma;

a decrease in HSP-72 within the lymphocytes.

By inducing an apoptotic-like state in the lymphocytes and other leucocytes in the blood comprising the autovaccine, as evidenced by the increased numbers of lymphocytes and other leucocytes exhibiting a condensed apoptotic-like morphology therein, these cells may become more readily phagocytosed upon re-injection into the host body.

There are a number of different phagocytic cell types present in the mammalian body, including various antigen presenting cells and neutrophils. In order to facilitate phagocytosis by antigen presenting cells rather than by other phagocytes, the lymphocytes and other leucocytes present in the autovaccine of the invention are treated so that they may interact preferentially with antigen presenting phagocytic cells. Cells adhere to each other by a number of mechanisms including the expression of cell adhesion molecules. Cell adhesion molecules present on one cell type interact with specific ligands for particular adhesion molecules present on the adhering cell type. The present invention may result in a preferential interaction of cells in the autovaccine to antigen presenting cells in the host body, by upregulation, on the surface of the cells in the autovaccine, of the expression of the ligand for adhesion molecules found on antigen-presenting cells in the host body. Antigen presenting cells express a number of cell adhesion molecules, including ICAM-1, a component of the ligand of which is CD-11b. One way by which the process of the invention may change the preferential phagocytosis of apoptosing cells is by upregulation of CD-11b.

The preparation of the autovaccine according to the present invention comprises extracting from the patient suffering from an autoimmune disease an aliquot of blood of volume about 0.01 ml to about 400 ml, and contacting the aliquot of blood, extracorporeally, with an immune system-stimulating effective amount of ozone gas and ultraviolet radiation.

The treatment for the alleviation of the symptoms of at least one autoimmune disease in a human patient suffering therefrom, in accordance with the present invention, comprises extracting from the patient an aliquot of blood of volume about 0.001 ml to about 400 ml, contacting the aliquot of blood, extracorporeally, with an immune system-stimulating amount of ozone gas and ultraviolet radiation, followed by administering the treated blood aliquot to the human patient.

BRIEF REFERENCE TO THE DRAWINGS

The accompanying drawing FIGURE is a graphical presentation of the results of Example 2 below.

DESCRIPTION OF THE PREFERRED EMBODIMENTS

When the autovaccine according to the present invention is injected into the autoimmune patient, significant alleviation of the patient's autoimmune condition is experienced, as set out in the specific embodiments of the invention described below. Exactly how the vaccine operates following this re-injection is not currently fully understood. The following tentative explanations are offered for a better and more complete description of the invention, but are not to be considered as binding or limiting.

T-cells, which are one kind of lymphocyte and which play a significant role in the control of the immune system, include CD-8 cells, and CD-4 cells otherwise known as T-helper cells, further subdividable into TH1 and TH2 cells. The TH1 cells secrete pro-inflammatory cytokines such as interferon gamma. The TH2 cells are considered to be regulatory cells and secrete regulatory cytokines, such as interleukin-4. In a normal, healthy individual, the ratio of TH1 cells to TH2 cells is around 3:1. In autoimmune conditions, there is usually an imbalance in the TH cell types, often with an increase in the TH1 cells compared to the TH2 cells, i.e. there is a change in the ratio between them, with a consequent development of an inflammatory condition often noted in autoimmune disease. A number of components of the autovaccine of the present invention, including HLA-DR and/or other MHC antigens released from the leucocyte cell surfaces, upregulate the TH2 cells in the patient's blood, thereby increasing the secretion of regulatory cytokines, and/or upregulating the suppressor cells to stimulate an inhibitory pathway for the autoimmune disease and alleviate or even switch off the autoimmune response pathway.

It is also commonly accepted that autoimmune disease sufferers may have significant populations of abnormal autoreactive T-cells, which are partly responsible for the autoimmune disease. The autoimmune disease suffering patient's ability to suppress these autoreactive T-cells is compromised. The autovaccine of the invention restores the system towards a normal immune state.

The autovaccine is prepared by exposing the blood aliquot to at least one stressor, in controlled amounts, the stressor being selected from among oxidizing agents such as ozone, ultraviolet radiation and elevated temperature, and combinations of two or more of such stressors. The resulting blood aliquot, after such treatment, serves as an autovaccine, and can be reinjected into the autoimmune patient. Following a course of such treatments, a patient's signs and symptoms of autoimmune disease such as those of rheumatoid arthritis, scleroderma and the like are markedly reduced. The subjective reports of alleviation of symptoms of rheumatoid arthritis are consistent with objective measurements of relative erythrocyte sedimentation rates, an objective test accepted as meaningful in measuring the progression of an autoimmune disease such as rheumatoid arthritis, by the American College of Rheumatology.

In preparing the autovaccine according to the invention, by modification of a blood aliquot extracted from the patient, the blood cells are stressed. This affects the heat shock proteins, HSP, contained in the cell. HSP-60 levels in the mononuclear cells are reduced, and are increased in the plasma. Further, the level of HSP-72 present in the mononuclear cells is reduced. Also as a result of the process of the invention, certain surface (membrane) proteins on the lymphocytes, for example HLA-DR, are reduced whereas others, such as CD-3, do not change and yet others such as CD-11b in neutrophils are upregulated. Accordingly it is apparently not a non-specific membrane change which is occurring, nor is it cell destruction. It is a complex active process.

On microscopic visualization of the autovaccine according to the present invention, mononuclear cells with a condensed apoptotic-like morphology can be observed, suggesting the presence in the autovaccine of increased numbers of apoptosing cells capable of preferential phagocytosis upon reinjection, for appropriate presentation of the antigens of the auto-immune disease.

In the preferred autovaccine in accordance with the present invention, the number of mononuclear cells or leucocytes exhibiting the presence of HSP-60 therein is decreased, as does the amount of HSP-60 in each cell, as compared with the normal, untreated peripheral blood of the source patient. Whereas the patient normally has, typically, about 30% of mononuclear cells exhibiting the presence of HSP-60 therein (as measured by whole blood intracellular flow cytometry), the autovaccine has only 12–20%. In clinical studies, it has been found that the figure reduces from 29.3% to 15.5%, mean of six tests. Preferably also, the number of leucocytes exhibiting the presence of HSP-72, which is about 50% in the untreated blood of the source patient, is reduced to 25–35% in the autovaccine of the present invention. In clinical studies, this figure for HSP-72 reduced from 49.4% in untreated blood to 30.2% in the autovaccine, mean of six tests, similarly measured.

The number of cells which express the cell surface specific protein HLA-DR, in the preferred autovaccine of the present invention, is reduced as compared with the patient's untreated blood, possibly as a result of its release from the cell surface. Typically, the number of cells expressing HLA-DR reduces from about 23% to about 8–12%, as measured by whole blood flow cytometry. In clinical studies, this figure reduced from 23.3% to 10.3%, mean of five experiments.

The upregulation of the surface marker CD-11b in the preferred autovaccine of the present invention can be expressed as an increase in the percentage of neutrophils in the autovaccine which test positive for CD-11b, compared with the patient's source blood. Typically, the increase is from about 10% up to the approximate range 70–95%. In clinical studies, an increase from 10.3% to 84% was obtained, mean of six tests.

A significant feature of the present invention is that the source of the blood from which the autovaccine is prepared for a specific patient suffering from an autoimmune disease is the patient himself or herself. The antigens forming the basis of the autovaccine find their origin in the patient's own blood. No extraneous antigens are added; the effective antigens are present in the patient's blood, and/or are released or modified by the process of preparing the autovaccine using the patient's own blood as the source material. Moreover, in many cases, the precise autoimmune disease from which the patient suffers appears to be immaterial. The antigens for the autovaccine for the disease are present in, or are developed by treatment of, the patient's own blood.

Preferably, the stressors to which the leucocytes in the extracted blood aliquot are subjected are a temperature stress (blood temperature above body temperature), an oxidative environment, such as a mixture of ozone and oxygen bubbled through the blood aliquot, and ultraviolet radiation, simultaneously or successively, but preferably simultaneously.

The present invention provides a method of alleviating the symptoms of an autoimmune disease in a human, which comprises:

(a) contacting of about 0.01 ml to about 400 ml of blood with an immune system modifying effective amount of ozone gas and ultraviolet radiation; and (b) administering the blood treated in step (a) to a human.

In general, from about 0.01 ml to about 400 ml of blood may be treated according to the invention. Preferred amounts are in the range of about 0.1 ml to 200 ml. More suitably, the aliquot for treatment has a volume of from about 0.1–100 mls, preferably 1–50 ml and most preferably 5–15 mls. The method most preferably involves treating an aliquot of about 10 mls of blood with ozone gas and ultraviolet radiation, then re-administering the treated blood to the patient by intramuscular injection.

As noted, it is preferred, according to the invention, to apply all three of the aforementioned stressors simultaneously to the aliquot under treatment. Care must be taken not to utilize an excessive level of the stressors, to the extent that the cell membranes of the white cells are caused to be disrupted.

The temperature stressor must keep the aliquot in the liquid phase, i.e. from about 0° C. to about 56° C. and should not heat it above about 55° C. Any suitable source of heat known in the art may be employed to heat the blood, preferably one or more infrared lamps. Preferably the temperature stressor warms the aliquot being treated, to a temperature above normal body temperature, i.e. to about 37–55° C., and most preferably from about 37–43° C., e.g. about 42.5° C. Preferably the temperature of the blood aliquot is maintained at this elevated temperature during the treatment with UV/ozone.

Alternatively, the blood sample is heated while being subjected to UV radiation, until the blood reaches a predetermined temperature (preferably about 42.5° C.), at which point bubbling of ozone gas through the blood is commenced. The concurrent UV/ozone treatment is then maintained for a predetermined period of time, preferably about 3 minutes.

Another alternative method involves subjecting the blood to UV/ozone while heating to a predetermined temperature (preferably about 42.5° C.), then either ending the treatment once the predetermined temperature is reached, or continuing UV/ozone treatment for a further period of time, most preferably about 3 minutes.

The application of the oxidative stressor preferably involves exposing the aliquot to a mixture of medical grade oxygen and ozone gas, most preferably by bubbling through the aliquot, at the aforementioned temperature range, a stream of medical grade oxygen gas having ozone as a minor component therein. The ozone gas may be provided by any conventional source known in the art. Suitably the gas stream has an ozone content of from about 1.0–100 $\mu$g/ml, preferably 3–70 $\mu$g/ml, and most preferably from about 5–50 $\mu$g/ml. The gas stream is supplied to the aliquot at a rate of from about 0.01–2.0 liters per minute, preferably 0.1–1.0 liters per minute and most preferably at about 0.12 liters per minute (STP).

The ultraviolet radiation stressor is suitably applied by irradiating the aliquot under treatment from an appropriate source of UV radiation, while the aliquot is maintained at the aforementioned temperature and while the oxygen/ozone gaseous mixture is being bubbled through the aliquot. The ultraviolet radiation may be provided by any conventional source known in the art, for example by a plurality of low-pressure ultraviolet lamps. The method of the invention preferably utilizes a standard UV-C source of ultraviolet radiation, namely UV lamps emitting in the C-band wavelengths, i.e. at wavelengths shorter than about 280 nm. Ultraviolet radiation corresponding to standard UV-A and UV-B sources can also be used. Preferably employed are low-pressure ultraviolet lamps that generate a line spectrum wherein at least 90% of the radiation has a wavelength of about 253.7 nm. An appropriate dosage of such UV radiation, applied simultaneously with the aforementioned temperature and oxidative environment stressors, is obtained from lamps with a power output of from about 15 to about 25 watts, at the chosen UV wavelength, arranged to surround the sample container holding the aliquot, each lamp providing an intensity, at a distance of 1 meter, of from about 45–65 mW/sq.cm. Several such lamps surrounding the sample bottle, with a combined output at 253.7 nm of 15–25 watts, operated at maximum intensity, may advantageously be used. At the incident surface of the blood, the UV energy supplied is 0.2–0.25 Joules per $cm^2$. Such a treatment provides a blood aliquot which is appropriately modified according to the invention to create the auto-vaccine outlined above ready for re-injection into the patient.

The time for which the aliquot is subjected to the stressors can be from a few seconds to about 60 minutes. It is normally within the time range of from about 0.5–60 minutes. This depends to some extent upon the chosen intensity of the UV irradiation, the temperature and the concentration of and rate at which the oxidizing agent is supplied to the aliquot. The more severe the stressors applied to the aliquot, generally the shorter time for which they need to be applied. Some experimentation to establish optimum times may be necessary on the part of the operator, once the other stressor levels have been set. Under most stressor conditions, preferred times will be in the approximate range of about 0.5–10 minutes, most preferably 2–5 minutes, and normally around 3 minutes. The starting blood temperature, and the rate at which it can be warmed or cooled to a predetermined temperature, tends to vary from patient to patient.

In the practice of the preferred process of the present invention, the blood aliquot (or the separated cellular fractions of the blood, or mixtures of the separated cells, including platelets, these various leucocyte-containing combinations, along with whole blood, being referred to collectively throughout as the "aliquot") may be treated with the stressors using an apparatus of the type described in U.S. Pat. No. 4,968,483 Mueller. The aliquot is placed in a suitable, sterile, UV-radiation-transmissive container, which is then fitted into the machine. The temperature of the aliquot is adjusted to the predetermined value, e.g. 42.5° C., by the use of a suitable heat source such as an IR lamp, and the UV lamps are switched on for a fixed period before the gas flow is applied to the aliquot providing the oxidative stress, to allow the output of the UV lamps to stabilize. Then the oxygen/ozone gas mixture, of known composition and controlled flow rate, is applied to the aliquot, for the predetermined duration of 0.5–60 minutes, preferably 2–5 minutes and most preferably about 3 minutes as discussed above, so that the aliquot experiences all three stressors simultaneously. In this way, the blood aliquot is appropriately modified to produce an auto-vaccine according to the present invention sufficient to achieve the desired effects.

Example 4 below supports the finding that the method of treating blood according to the invention has an immune modifying effect. In particular, treatment of blood with UV/ozone has been found to increase the expression of activation markers on the surface of the lymphocytes (see Example 5).

Thus, the invention also provides a method of stimulating or activating the immune system in a human by contacting about 0.01 ml to about 400 ml of blood from a human with an immune system-stimulating effect amount of ozone gas and ultraviolet radiation, followed by administering the treated blood to a human. Similarly, the invention contemplates a method of treating an immune system disorder in a human, by contacting about 0.01 ml to about 400 ml of blood from a human with an immune system-stimulating effective amount of ozone gas and ultraviolet radiation, followed by administering the treated blood to a human.

The immune system disorders which may be treated by this method include allergic conditions, autoimmune conditions, and an inflammatory conditions. Specific immune system disorders which may be treated according to the invention include rheumatoid arthritis, scleroderma, diabetes mellitus, organ rejection, miscarriage, multiple sclerosis, inflammatory bowel disease, psoriasis, and other inflammatory disorders. The discoveries of the present invention may also be applied to treat autoimmune diseases which manifest as infertility, including endometriosis. It is also effective in treatment of atherosclerosis, which can be regarded as an autoimmune disease of the vasculature.

The invention is further described for illustrative purposes with reference to specific examples of clinical use of it and objective and subjective results from such clinical uses.

SPECIFIC DESCRIPTION OF THE MOST PREFERRED EMBODIMENTS

EXAMPLE 1

Thirty patients with active rheumatoid arthritis, 21 females and 9 males, were treated by the preferred process according to the present invention. The age range of the patients was 26–72 years, with the mean age 52.2 years, at the start of the study. Each patient received between 30 and 60 individual treatments (mean 48.3 treatments) over a time span of 62 weeks (mean 20.6 weeks). Each individual treatment consisted of the removal of a 10 mL aliquot of blood, the treatment of the blood aliquot simultaneously with gaseous oxygen/ozone mixture and ultraviolet light at elevated temperature using an apparatus as generally described in the aforementioned U.S. Pat. No. 4,968,483 Mueller et.al.

The constitution of the gas mixture was 14–15 mcg/mL ozone/medical grade oxygen. The gas mixture was fed through the aliquot at a rate of about 200 mLs/minute, for a period of 3 minutes. The temperature of the aliquot was held steady at 42.5° C. The UV radiation had a wavelength of 253.7 nm.

Post treatment measurements were conducted 1 day to nine months after the final treatment of each patient (mean 12.4 weeks). Blood samples were taken and analyzed for leucocytes, erythrocyte sedimentation rate, rheumatoid factor and C-reactive protein, using standard test procedures. The erythrocyte sedimentation rate and C-reactive protein are elevated in most inflammatory conditions including rheumatoid arthritis, and Rheumatoid Factor is elevated in most cases of rheumatoid arthritis as well as in some cases of certain other auto-immune diseases. White blood cell count, erythrocyte sedimentation rate, rheumatoid factor and C-reactive protein all showed significant reduction after the course of treatment. Particularly noteworthy is the significant reduction in erythrocyte sedimentation rate, an indicator of rheumatoid arthritis improvement, accepted by the American College of Rheumatology.

In addition, patients were rated by medical personnel subjectively, for the apparent severity of their rheumatoid arthritis symptoms, before and after the courses of treatment, on a scale of 5 (very bad) to 1 (excellent). Again, a marked improvement in each case was reported.

The mean results are given in the following Table.

TABLE

| Clinical Measurements | Normal Ranges | (Pre-Treatment Mean ± SD) | Post-Treatment (Mean ± SD) | Paired T-test |
|---|---|---|---|---|
| Symptom Rating | | 3.9 ± 0.9 | 2.6 ± 0.6 | $p < 0.0001$ |
| Leucocytes $10^9$/L | 4.0–10.0 | 11.68 ± 2.84 | 8.70 ± 1.02 | $p < 0.0001$ |
| Erythrocyte Sed. Rate 1 hr (mm) | 0–20 | 50.1 ± 22,9 | 28.1 ± 13.7 | $p < 0.0001$ |
| Rheumatoid Factor iu | <100 | 117.0 ± 76.1 | 91.7 ± 67.4 | $p < 0.02$ |
| C-Reactive Protein mg/L | <1.0 | 5.28 ± 3.62 | 3.73 ± 3.44 | $p < 0.009$ |

EXAMPLE 2

Four patients with primary Raynaud's disease were given a course of therapy according to the invention, in an open clinical trial performed at St Bartholomew's Hospital, London, under properly controlled and supervised conditions. All four patients showed alleviation of their symptoms following treatment.

An investigation of an autoimmune component of the disease in these patients demonstrated high levels of auto-antibodies specific for HSP-60 and HSP-65 in one patient. The levels of these auto-antibodies in this patient are shown on the accompanying FIGURE, from which it can be seen that the levels decreased markedly following a course of therapy. The first course of treatment, indicated "1" on the FIGURE, consisted of 9 treatments carried out over 14 days. Furthermore, the levels of these auto-antibodies began to increase again some weeks later, and were again lowered following a second course of therapy. The second course of treatment, indicated "2" on the FIGURE, consisted of 5 treatments carried out over 10 days. These data suggest that therapy with blood treated according to the invention, i.e. the autovaccine described herein, may reduce an autoimmune response as evidenced by a reduction of auto-antibodies in a treated patient.

EXAMPLE 3

The helper T-lymphocyte subsets TH1 and TH2 have been measured in 13 normal control volunteers and in two patients suffering from the autoimmune disease scleroderma. The ratio of TH1:TH2 in the controls, as measured by intracellular cytokine flow cytometry, was found to be 3.029+/−0.639 (mean +/− standard deviation). The patients with scleroderma had TH1:TH2 ratios of 5.0 and 4.58 respectively, most likely, indicating an increase in the TH1 population relative to the TH2 population. In inflammatory pathologies such as many autoimmune diseases there is a relative increase in the TH1 cells; therefore it was to be expected that this ratio would be higher in these patients than in the healthy control individuals.

Following a course of therapy with blood treated according to the invention (i.e. the autovaccine described herein), the TH1:TH2 ratios in these patients was 3.29 and 3.13 respectively, i.e. the ratio had approached the normal range. These data suggest that therapy with blood treated according to the present invention may reduce an autoimmune response as evidenced by a relative increase in the TH2 cells.

EXAMPLE 4

STAINING OF ACTIVATION MARKERS

This example illustrates an experimental approach which indicates that treatment of blood with UV/ozone according to the invention has an immune-stimulatory effect on human blood, as evidenced by an increase in certain activation markers on the surface of the treated mononuclear cells.

Samples (20 ml) of peripheral blood were taken from individuals. Each sample was divided into two aliquots. The first aliquot was treated according to the inventive technique, as follows:

The 10 ml aliquot was treated in vivo for three minutes with ozone gas (variable ozone concentration of 5–50 µg/ml) and ultraviolet light (253.7 nm), at a temperature of 42.5° C. An apparatus similar to that disclosed in U.S. Pat. No. 4,968,483 was utilized to carry out the treatment of the blood sample.

The second 10 ml aliquot from each sample served as an untreated control.

Each blood sample was stained for certain activation markers of T-lymphocytes using conventional monoclonal antibody techniques. The proportion of the total cells which stained positive for the individual markers was quantitated by microscopy. The results are as follows:

| Marker | Control | Ozone/UV Treated |
|---|---|---|
| CD25 (IL-2 receptor) | 1% | 26% |
| CD2 (E-rosette receptor) | 3% | 33% |

The above data for this example are all means of duplicates, and indicate that treatment with UV/ozone according to the invention results in the activation of T-lymphocytes.

I claim:

1. A process of treating a mammalian patient suffering from an autoimmune disease, to alleviate the symptoms thereof, which comprises:

extracting an aliquot of blood from a patient;

modifying the extracted blood aliquot extracorporeally by subjecting it to an immune system-modifying amount of ozone gas and ultraviolet radiation, so as to create in the blood aliquot, in comparison with an equal volume aliquot of said patient's unmodified blood, at least one of the following distinguishing features:

(a) increased numbers of leukocytes exhibiting a condensed apoptotic-like morphology;

(b) a reduction in the number of leukocytes expressing the MHC Class II leukocyte cell surface specific protein HLA-DR;

(c) an upregulated expression on leukocytes of the CD-11b cell surface marker and re-injecting the blood aliquot so modified into said patient.

2. The process of claim 1 wherein the aliquot size is from 0.01–400 ml.

3. The process of claim 2 wherein the aliquot size is from 1–50 ml.

4. The process of claim 1 wherein the ozone gas and ultraviolet radiation are applied to the blood aliquot simultaneously, whilst the blood aliquot is at a temperature of from 37–55° C.

5. The process of claim 1 wherein the ozone is administered as a gas stream in admixture with medical grade oxygen, the ozone content therein being from 0.5–100 µg/ml, at a rate of from 0.01–2.0 liters per minute (STP), over a period of 0.5–60 minutes.

6. The process of claim 1 wherein the ultraviolet radiation is supplied from at least one ultraviolet lamp emitting in the C-band wavelength.

7. The process of claim 1 wherein the ultraviolet radiation is obtained from ultraviolet lamps emitting at least about 90% of ultraviolet radiation of a wavelength about 253.7 nm.

8. The process of claim 5 wherein the blood aliquot is treated with ozone and ultraviolet radiation at a temperature from 37–43° C., for a period of from 2–5 minutes, the ozone/oxygen mixture being supplied at a rate of from 0.1–1.0 liters per minute, with an ozone content of from 5–50 µg/ml.

9. The process of claim 1 wherein the autoimmune disease is arthritis.

10. The process of claim 8 wherein the autoimmune disease is rheumatoid arthritis.

11. The process of claim 1 wherein the autoimmune disease is scleroderma.

12. The process of claim 1 wherein the extracted blood aliquot is extracorporeally treated so as to additionally create in the patient's peripheral blood after re-injection, in comparison with said patient's unmodified peripheral blood, a decrease in the ratio of TH1:TH2 cells.

* * * * *